(12) United States Patent
Blackledge

(10) Patent No.: US 9,507,178 B1
(45) Date of Patent: Nov. 29, 2016

(54) ELECTROMAGNETIC WAVEGUIDE ASSEMBLY

(71) Applicant: Charles Wesley Blackledge, Berlin (DE)

(72) Inventor: Charles Wesley Blackledge, Berlin (DE)

( * ) Notice: Subject to any disclaimer, the term of this patent is extended or adjusted under 35 U.S.C. 154(b) by 0 days.

(21) Appl. No.: 14/468,848

(22) Filed: Aug. 26, 2014

Related U.S. Application Data

(60) Provisional application No. 61/871,322, filed on Aug. 29, 2013.

(51) Int. Cl.
*G02F 1/025* (2006.01)
*G02F 1/01* (2006.01)

(52) U.S. Cl.
CPC ..................... *G02F 1/011* (2013.01)

(58) Field of Classification Search
CPC .... G02F 1/025; G02F 1/0147; H04B 10/505
USPC ..................... 385/1; 356/301, 480
See application file for complete search history.

(56) References Cited

U.S. PATENT DOCUMENTS

| | | | |
|---|---|---|---|
| 6,490,039 B2 | 12/2002 | Maleki et al. | |
| 6,657,731 B2 * | 12/2003 | Tapalian et al. | 356/480 |
| 7,933,022 B2 * | 4/2011 | Smith et al. | 356/480 |
| 8,080,183 B2 * | 12/2011 | Kotov et al. | 252/519.4 |
| 8,493,560 B2 * | 7/2013 | Shopova et al. | 356/301 |
| 8,670,476 B2 * | 3/2014 | Goddard et al. | 372/64 |
| 2004/0137478 A1 * | 7/2004 | Arnold et al. | 435/6 |
| 2009/0116788 A1 * | 5/2009 | Rakich | B82Y 20/00 385/32 |
| 2012/0069331 A1 | 3/2012 | Shopova | |
| 2012/0281957 A1 * | 11/2012 | Chamanzar | B82Y 20/00 385/131 |
| 2015/0017433 A1 * | 1/2015 | Alisafaee et al. | 428/338 |
| 2015/0285728 A1 * | 10/2015 | Ozdemir | G01N 15/1434 356/301 |

OTHER PUBLICATIONS

Alex Kaplan et. al. "Finite element simulation of a perturbed axial-symmetric whispering-gallery mode . . . ," Optics Express V. 21 pp. 14169-14180; Jun. 27, 2013.
Wonmi Ahn et. al. "PhotonicPlasmonic Mode Coupling in On-Chip Integrated Optoplasmonic Molecules," ACS Nano V. 6, pp. 951-960; Dec. 8, 2011.
Wonmi Ahn et. al, "Demonstration of Efficient On-Chip Optoplasmonic Networks." ACS Nano V. 7, pp. 4470-4478; Apr. 19, 2013.
E. Gavartin et. al "A hybrid on-chip optomechanical transducer for ultrasensitive force measurements," Nature Nanotechnology V. 7, pp. 509-514; Jun. 24, 2014.
Dries Van Thourhout et. al. "Optomechanical device actuation through the optical gradient force," Nature Photonics V. 4, pp. 211-217; Mar. 31, 2010.
Xiaodong Yang et. al. "Optical Forces in Hybrid Plasmonic Waveguides," Nano Letters V. 11, pp. 321-328; Jan. 13, 2011.
J. F. Tao et. al. "On-chip optical power measurement by optical force," Transducers' 11 IEEE, pp. 1911-1914; Possibly Jun. 9, 2011, unknown exact date.

(Continued)

Primary Examiner — Ellen Kim

(57) ABSTRACT

An electromagnetic waveguide assembly is disclosed, which includes a microresonator and a perturbative member. A gap is between the perturbative member and the nearest surface of the microresonator. The perturbative member is within a range for perturbing the electromagnetic wave supported by the microresonator.

20 Claims, 11 Drawing Sheets

(56) References Cited

OTHER PUBLICATIONS

Matthew S. Luchansky et. al. "High-Q Optical Sensors for Chemical and Biological Analysis," Anal. Chem V. 84 pp. 793-821; Nov. 23, 2011.

G. Anetsberger et. al. "Near-field cavity optomechanics with nanomechanical oscillators," Nature Physics V. 5 pp. 909-914, Oct. 11, 2009.

A. Schliesser et. al. "High-sensitivity monitoring of micromechanical vibration using optical whispering gallery mode" arXiv:0-805.1608c1 [quant-ph], pp. 1-25, May 12, 2008.

Onur Basarir et. al, "Sensitive meieromechanical displacement detection . . . " Optics Letters V. 35 No. 11, pp. 1792-1794; Jun. 1, 2010.

Min Ren et. al, "Nano-optomechanical Actuator . . . " ACS Nano V. 7 No. 2, pp. 1676-1681; Jan. 25, 2013.

G. C. Righini et. al. "Whispering gallery mode microresonators . . . " Rivista del nuovo cimento V. 34 No. 7, pp. 435-488; ricevuto il Mar. 30, 2011.

V. R. Dantham et. al, "Taking whispering gallery-mode . . . to the limit," Applied Physics Letters V. 101, pp. 043704-1 to 043704-4. Jul. 27, 2012.

Martin Baaske et. al. "Optical Resonator Biosensors . . . " ChemPysChem V. 13, pp. 427-436, likely published in 2012.

Maysamreza Chamanzar et. al. "Hybrid nanoplasmonic-photonic resonators . . . " Optics Express V. 19, No. 22, pp. 22292-22304; Oct. 24, 2011.

Victor Fiore, Chunhua Dong, Mark. C. Kuzyk, Hailin Wang. "Optomechanical light storage in a silica microresonator" the internet, unknown date. Dept. of physics, U. of Oregon.

Fang Ren et. al, "Second Harmonic Generation . . . resonator," Proc. of SPIE V. 8463, 846305. Oct. 15, 2012.

C. Ciminelli et. al. "Design of an optical trapping device . . . structure . . . " IEEE Photonics Journal V. 6 No. 6, 0600916, Dec. 2014.

Yin Zhang-Qi et. al. "Hybrid opto-mechanical systems with nitrogen-vacancy centers." Science China, Physics, Mechanics & Astronomy; Jan. 4, 2015.

Yangcheng Li et. al. "Demonstration of whispering-gallery-mode resonant enhancement of optical forces." IEEE 2014 National Aerospace adn Electroncis Conference (NAECON), Dayton, Ohio, Jun. 2014.

Jing Chen et. al. "Tunable Resonances in the Plasmonic SPlit-Ring Resonator." IEEE Photonics Journal. vol. 6, No. 3, 48010706,Jun. 2014.

Yang Xiong et. al. "Coupled Photonic Systems Between Core-Shell Nanoparticle and Integrated Microresonator." IEEE Journal of Quantum Electroncs, vol. 50, No. 8 677-682. Aug. 2014.

Andrey B. Matsko and Lute Maleki. "Feshbach Resonanaces in Kerr Frequency Combs." arXiv:1410.8604v1 [physics.optics] Oct. 31, 2014.

Philip A. Laplante, Editor. "Electrical Engineering Dictionary." CRC Press. Boca Raton: CRC Press LLC, 2000.

Stan Gibilisco, "The Illustrated Dictionary of Electronics, 8th Edition." McGraw-Hill. 2001. ISBN 0-07-137236-9.

Yan et. al. "Controlling the position and orientation of single silver nanowires on a surface using structured optical fields." ACS Nano. 2012, 6 (9), 8144-8155.

S. Goetzinger et al. "Mapping and manipulating whispering gallery modes . . . with a near-field probe." Journal of Microscopy. V. 202 (1). pp. 117-121. 2001.

M. Ostrowski et al. "Higher order optical resonance node detection of integrated disk micro resonator." Optics Letters. arxiv.org, Jun. 29, 2011.

M. Chamanzar and Ali Adibi. "Hybrid nanopasmonic-photonic resonators . . . " Optics Express, V. 19 No. 22, 22292. Oct. 24, 2011.

W. Liang et al. "Ultralow noise miniature external cavity semiconductor laser." Nature Communications. 6:7371 doi: 10.1038/ncomms8371. Jun. 24, 2015.

A. Schliesser et al. "Cavity optomechanics with whispering-gallery mode optical micro-resonators." arxiv:1003.5922v1. Mar. 30, 2010.

D. Armani et al. "Electrical thermo-optic tuning of . . . resonators." Applied Physics Letters, V. 85 No. 22. pp. 5439-5441. Nov. 29, 2004.

Jiangang Zhu et al. "Interfacing whispering-gallery microresonators and free space light . . . " Scientific Reports. vol. 4, 6396. Sep. 17, 2014.

C. Ciminelli et al. "Design of an optical trapping device based on an ultra-high Q/V resonant structure." IEEE Photonics Journal. vol. 6, No. 6, 0600916. Dec. 2014.

S. I. Shopova et al. "Enhanced evanescent couplig . . . microresonator surface." Applied Physics B .vol. 93: 183-187. Aug. 28, 2008.

Svetlana V. Boriskina et al. "Molding the flow of light on the nanoscale . . . " Nanoscale, 2012, 4, 76. Jan. 7, 2012.

Miguel A. Santiago-Cordoba et al. "Ultrasensitive detection . . . in a photonic-plasmonic microcavity." Journal of Biophotonics. 1-10 (2012). Jun. 15, 2012.

Alex Kaplan et al. "Finite element simulation . . . nanoparticle coupled to a microtoroid." Optics Express. vol. 21, issue 12, pp. 14169-14180. Jun. 17, 2013.

Maysamreza Chamanzar et al. "Hybrid nanoplasmonic-photonic resonators . . . " Optics Express. vol. 198, No. 22, 22292. Oct. 24, 2011.

M. Ostrowski et al. "Higher order optical resonance . . . of integrated disk micro resonator." Optics Letters. vol. 36, Issue 16, pp. 3042-3044. Aug. 15, 2011.

S. I. Shopova et al. "Plasmonic enhacement of . . . biosensor for single nanoparticle detection." Applied Physics Letters. 98, 243104(2011). Jun. 13, 2011.

Manas Ranjan Gartia et al. "Injection-seeded optoplasmonic amplifier . . . " Scientific Reports, 4, 6168. Aug. 26, 2014.

S. Goetzinger et al. "Mapping . . . a microsphere resonator with a near-field probe." Journal of Microscopy. vol. 202, Pt. 1, pp. 117-121. Apr. 2001.

Yan Hong et al. "Enhanced Light Focusing . . . with Subwavelength Dimensions." Advanced Materials. vol. 25, Issue 1. pp. 115-119. Jan. 4, 2013.

Wonmi Ahn et al. "Demonstration of Efficient On-Chip Photon Transfer in Self-Assembled Optoplasmonic Networks." ACS Nano vol. 7 (5), pp. 4470-4478. Apr. 19, 2013.

Matthew R. Foreman et al. "Whispering Gallery Mode Sensors." Advances in Optics and Photonics. vol. 7. pp. 168-240.May 22, 2015.

Jiangang Zhu et al. "Controlled manipulation of mode splitting in an optical microcavity by two Rayleigh scatterers." Optics Express. vol. 18, No. 23. 23536. Nov. 8, 2010.

Joachim Knittel et al. "Back-scatter based whispering gallery mode sensing." Nature, Scientific Reports. 3 : 2974. Oct. 17, 2013.

* cited by examiner

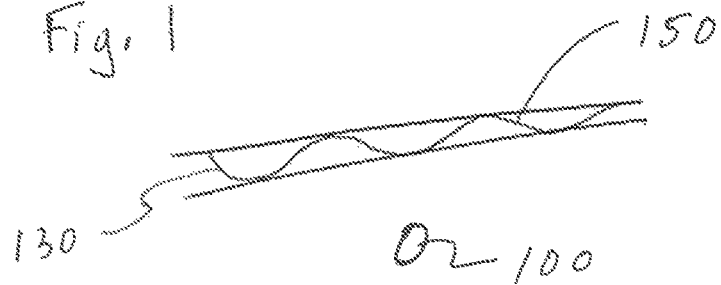
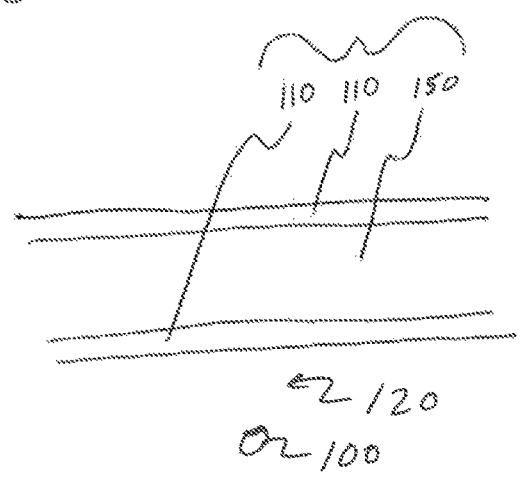
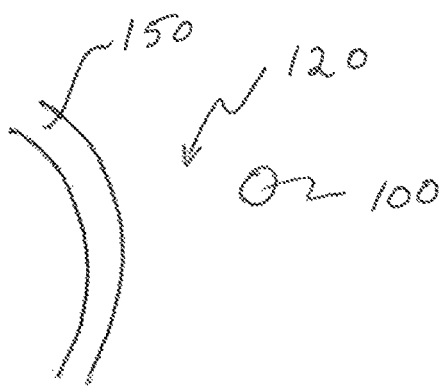

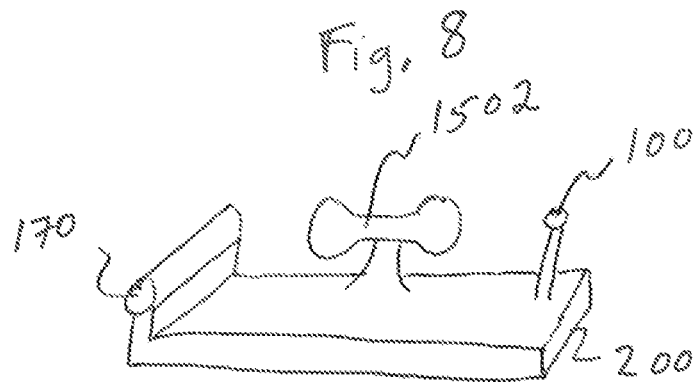
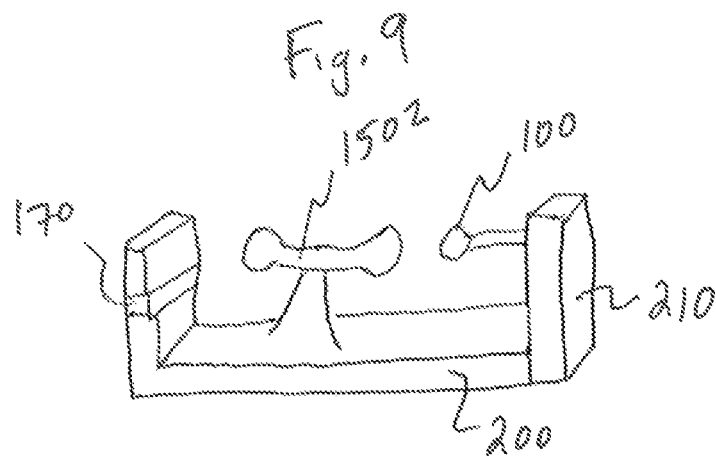
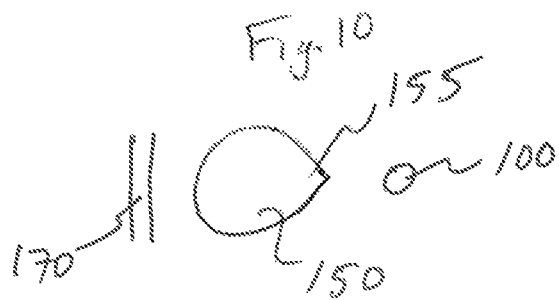
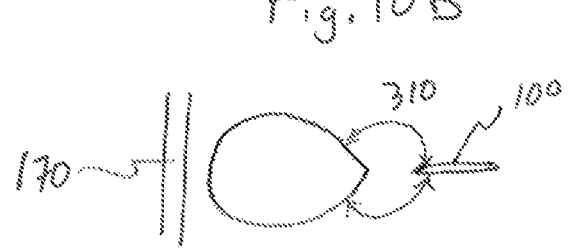

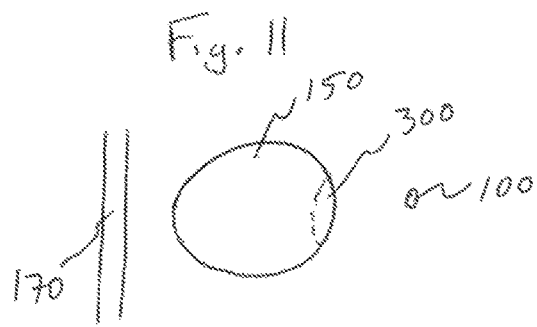
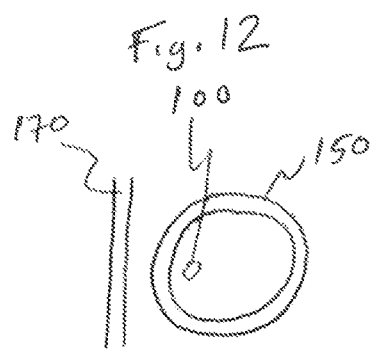
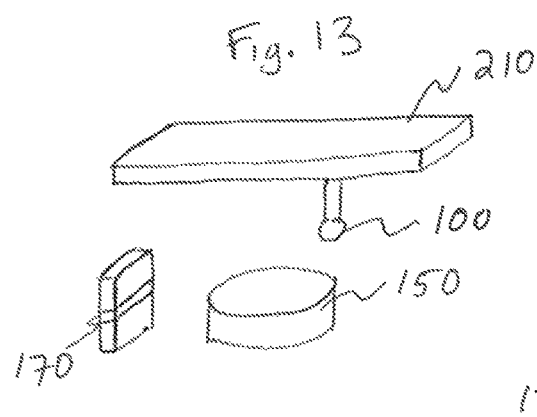
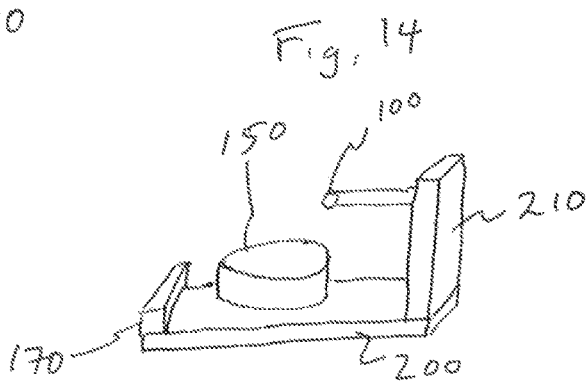
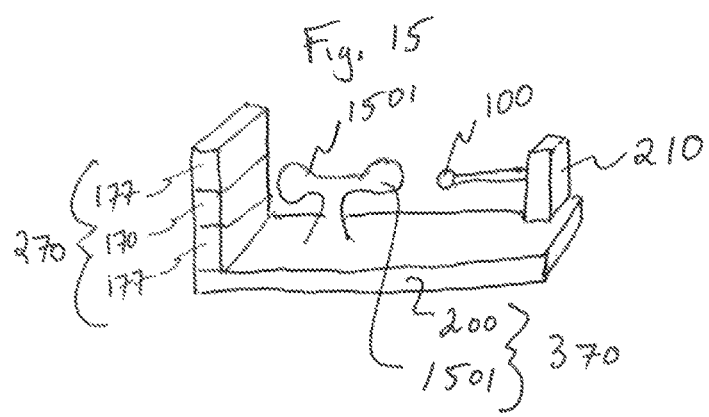

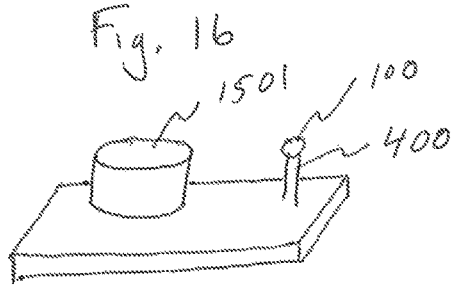
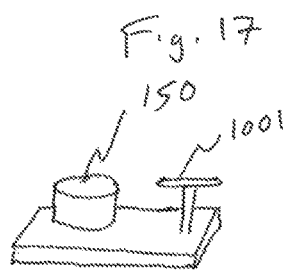
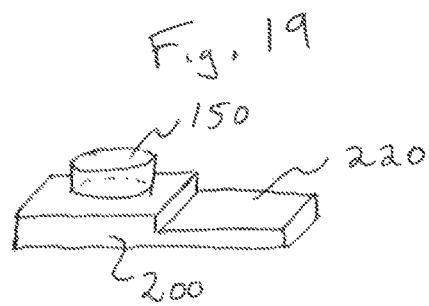
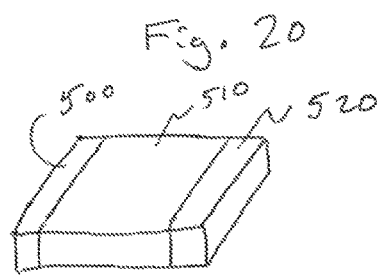
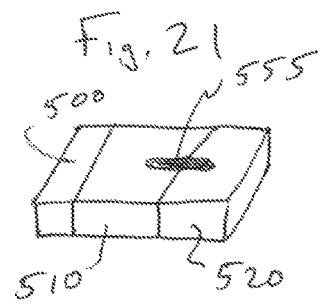
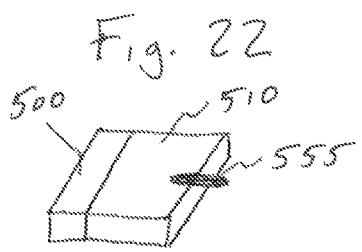
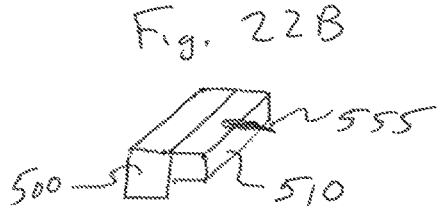
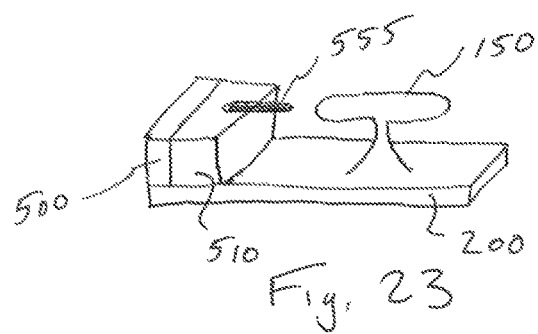

ELECTROMAGNETIC WAVEGUIDE ASSEMBLY

This application claims the benefit of U.S. Provisional Application 61/871,322, filed Aug. 29, 2013, the contents of which are incorporated by reference in their entirety.

FIELD OF THIS DISCLOSURE

The present disclosure relates to small electromagnetic resonators, and to associated methods of use as sensors and modulators for example.

BACKGROUND

There is a desire for miniaturization of components for the manipulation of electromagnetic energy such as for providing sensitive sensors and/or optical devices. Microresonators can be used as sensors and electromagnetic switches for example.

SUMMARY

An electromagnetic waveguide assembly is disclosed herein, comprising a microresonator for supporting an electromagnetic wave, the microresonator including a waveguide, a bus waveguide for coupling with the microresonator, a perturbative member for perturbing the electromagnetic wave, a support for supporting the perturbative member; and a gap between a nearest surface of the perturbative member and a nearest surface of the microresonator, the nearest surfaces being the nearest surfaces of the respective perturbative member and the microresonator to each other, the gap being such that the perturbative member is within a range for perturbing the electromagnetic wave.

A waveguide assembly is disclosed herein, comprising a waveguide for supporting an electromagnetic wave, and a polymer filament. The polymer filament includes a molecularly coded region for binding a complementarily molecularly coded species; the coded region disposed at a distance from a nearest surface of the waveguide, the distance being greater than 1 nm; the coded region disposed within an evanescent region of the supported electromagnetic wave.

A method of operating an optical device is disclosed herein, comprising inputting an input EM wave such that the input EM wave optically couples to a microresonator and a supported EM wave is formed which is supported by the microresonator; perturbing the supported EM wave by a perturbative member located across a gap from a nearest surface of the microresonator; outputting the supported EM wave to form an output EM wave; and detecting the output EM wave; optionally modulating the perturbative member such as driving a mechanical oscillation of the perturbative member; wherein optionally modulating the perturbative member includes modulating the input EM wave such that the perturbative member is modulated; optionally modulating, such as pulsing, the input EM wave such that the position of the perturbative member is modulated; optionally binding an analyte near the perturbative member; wherein optionally detecting the output EM wave includes mixing the output EM wave with a reference EM wave such as the input EM wave; optionally positioning the perturbative member, particularly adjusting the gap; wherein optionally positioning the perturbative member is with an actuator and/or an intensity such as a continuous wave intensity component of the input EM.

BRIEF DESCRIPTION OF THE DRAWINGS

FIG. 1 shows a waveguide, an electromagnetic wave, and a perturbative member, according to embodiments described herein.

FIGS. 2 and 3 show a waveguide and perturbative member, each according to embodiments described herein.

FIGS. 4, 5, 6, 7, 8, 9, 10, 10B, 11, 12, 13, 14, and 15 show a waveguide assembly, each according to embodiments described herein.

FIGS. 16, 17, and 18 show a perturbative member and a resonator, each according to embodiments described herein.

FIG. 19 shows a resonator, according to embodiments described herein.

FIGS. 20, 21, 22, and 22B show components for forming an electromagnetic waveguide assembly, each according to embodiments described herein.

FIG. 23 shows a bus waveguide buried under a resonator, according to embodiments described herein.

DETAILED DESCRIPTION

Figure 4:
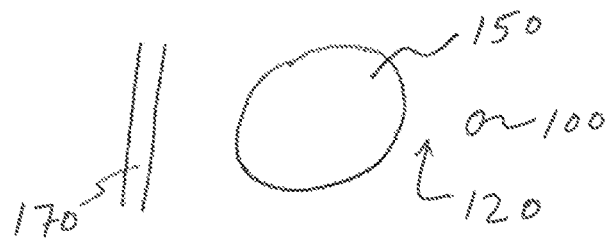

FIG. 1 shows a waveguide 150 along which an electromagnetic wave 130 such as an optical signal can be supported, for example a propagating and/or standing electromagnetic wave. The waveguide provides an evanescent region which extends beyond the boundary of the waveguide. When an electromagnetic wave passes through the waveguide, an evanescent field exists in the evanescent region. For a waveguide in a surrounding such as a uniform medium such as air or a polymer cladding, as distance from the interface between the waveguide and its surrounding increases, the intensity of the electromagnetic field intensity decreases exponentially. A waveguide may transmit fully the electromagnetic energy through the waveguide, although it is also possible for some absorption and/or scattering in materials used as waveguides, typically silica, glass, or silicon. In embodiments disclosed herein, a perturbative member 100 can be located within the evanescent region. The perturbative member can perturb the propagation of the electromagnetic wave, for example by altering the path of the electromagnetic wave, altering the pathlength, altering the mode and/or modal density of the electromagnetic wave, altering the spatial distribution of the mode volume of the electromagnetic wave, and/or inducing scattering, absorption and other optical effects.

As shown in FIG. 2, a perturbative member 100 can be located away from a nearest surface of a waveguide assembly 160, the assembly 160 including a waveguide 150 and optionally a coating 110. FIG. 2 shows a gap 120 between the waveguide assembly 160 and a perturbative member 100. For example, a travelling electromagnetic wave propagating through the waveguide has an evanescent component that extends beyond the boundary of the waveguide assembly. It is appreciated that if a coating is present, its thickness is small enough to allow the evanescent field to extend (appreciably) beyond the boundary of the waveguide assembly; alternatively or additionally the difference of the indices of refraction of the coating and the waveguide may be small enough to allow the evanescent field to extend beyond the boundary of the waveguide assembly. The gap 120 can allow for the binding of an analyte at some distance away from the surface of the waveguide assembly 160, allowing electromagnetic energy to interact with the analyte; alternatively or additionally, the gap can provide for a cooling media such as a fluid, e.g. a gas or fluid which includes an analyte, to be disposed between the waveguide assembly and the perturbative member.

For example a thickness of approximately 5 nm, 10 nm, 50 nm, 100 nm, or 150 nm of a polymer such as polydimethylsiloxane and/or PMMA on a silica waveguide can be used as a coating 110. A coating is desirable for example to protect the waveguide from contamination.

An optional coating on the waveguide is contemplated for example an outermost coating such as one including polyethylene glycol, fluorocarbons, and/or other surface functionalities that are resistant to adsorption of contaminants such as biomolecules which may bind nonspecifically to the waveguide assembly and cause interfering and/or irreversible perturbations to the electromagnetic wave. For example, if the waveguide assembly is part of a microresonator, nonspecific binding for example of contaminants and/or analytes may cause irreversible changes to the electromagnetic resonances of the microresonator, e.g. reducing throughput, shifting the resonant frequency or frequencies, and/or reducing the quality factor.

Furthermore, a coating may counteract thermal heating effects of the electromagnetic wave on the optical properties of the waveguide. For example, if the waveguide assembly is part of an electromagnetic microresonator, electromagnetically generated heat can perturb the index of refraction of the waveguide and/or expand the microresonator, increasing the optical pathlength thus perturbing resonant optical mode, for example shifting the resonant frequency. Reduction and/or compensation of such thermal effects of electromagnetic waves in microresonators by the use of coatings is possible.

A drawback of a thick coating is that it can increase the distance from the perturbative member to the waveguide. For example an increased distance results in a decrease in the EM field strength at the location of the perturbative member. It is appreciated that herein, the coating may not be shown in every drawing, but may nevertheless be present in any embodiment described herein.

In FIG. 3, the waveguide 150 is curved, which may increase the fraction of evanescent component of an electromagnetic wave supported by the waveguide. The perturbative member 100 can be located such that the nearest surface of the waveguide 150 is a curved surface, with a local radius of curvature of for example 0.05, 0.1, 0.25 0.5, 1, 2, 4, 6, 8, 10, 10 to 30, 35, 40, 45, 50, 55, 60, 65, 70 to 100 micrometers, or from 10 to 150 micrometers. The local radius of curvature can be smaller than the radius of curvature of the waveguide elsewhere, which can increase the fraction of modal density in the vicinity of the perturbative member. For example, the nearest surface of the microresonator to the perturbative member is curved with a curvature greater than the average curvature of the microresonator. A gap between the nearest surface of the waveguide 150 or waveguide assembly 160 (optionally including a coating) and the perturbative and/or binding region/site thereof is at least about 1 nm, or 2 nm, 3 nm, 4 nm, 5 nm, 6, 7, 8, 9, or 10 nm, or 12, 14, 16, 18, or 20 nm, or 25, 30, 35, 40, 45, 50 55, 60, or 70, 80, 90, 100, 120, 140, 160, 180, 200, or from 200 to 500 nm, or 500 to 1000 nm.

It is desirable to have a small gap 120 between the perturbative member 100 and the nearest surface of the waveguide, although at small distances, a travelling electromagnetic wave may provide a strong enough attractive optical gradient force to the perturbative member as to cause the perturbative member to move and make contact with the waveguide or waveguide assembly. In many applications of waveguide assemblies, it is desirable to avoid contact of the perturbative member with the waveguide assembly, for example to allow adjustment and or control of the gap to provide a modulation of the perturbative effect of the perturbative member on the travelling wave (by modulating the gap distance for example); alternatively or additionally a gap 120 may provide a position for a binding site and/or binding region which lies between the perturbative member and the waveguide assembly, this position being a region of comparatively high electromagnetic intensity yet accessible to an analyte. It is also contemplated that in some embodiments, the perturbative member 100 may make intermittent and/or periodic contact with the waveguide assembly, particularly if the perturbative member is actuated such as by periodic actuation. For example, the perturbative member can be a driven mechanical oscillator. For example, mechanical oscillations of the perturbative member can be driven by optical field gradients, e.g. provided by an electromagnetic wave such as one supported by the nearby waveguide 150; by a piezoactuator for example operatively coupled to the perturbative member; and by acoustic waves; etc. The gap distance can be adjustable, such as by using an actuator.

The perturbative effect of the perturbative member on the travelling electromagnetic wave is reduced as the distance of the perturbative member from the boundary of the waveguide is increased, i.e. due to the decaying evanescent field intensity. Where the evanescent field is stronger, the perturbative effect of the perturbative member on the electromagnetic wave is greater, thus it is favorable to have a thin or no coating on the waveguide in the vicinity of the perturbative member so as to decrease the distance from the boundary of the waveguide to the perturbative member. However, there is a benefit of avoiding contamination and/or heating effects (which may alter the pathlength of the waveguide) with the presence of an appropriate coating. It is noted that the spatial intensity decay of the evanescent wave is not so sharp as to exclude perturbative effects of a perturbative member at positions of tens or even hundreds of nanometers from the nearest surface of the waveguide, and it is further noted that the spatial decay length of the evanescent field depends on the wavelength of the electromagnetic wave.

FIG. 4 shows a waveguide 150 in the form of a resonator, for example a disc, toroid, ring, ellipsoid, sphere, etc. A resonant electromagnetic mode such as an optical mode may be supported by the resonator, e.g. a mode internally reflected at the surface of the waveguide, the pathlength of the supported mode being an integer multiple of the wavelength of the electromagnetic wave. Whispering gallery modes are particularly contemplated. A bus waveguide 170 can couple the electromagnetic wave into and/or out of the resonator. Many different types of bus waveguides are possible, e.g. a tapered optical fiber positioned near the resonator, a strip waveguide, and a buried waveguide (e.g. buried in the support beneath the resonator and vertically coupled to the resonator). A perturbative member 100 is shown which can perturb the electromagnetic modes supported by the resonator. A gap 120 is disposed between the nearest surface of the waveguide 150 and the perturbative member 100. The bus waveguide 170 can be under, over, or critically coupled to the waveguide. For example, critical coupling may lead to efficient energy storage in a resonator 150 of electromagnetic energy which may be input by the bus waveguide 170. In another example, an overcoupled arrangement is expected to allow for efficient collection of signal generated by an electromagnetic wave such as an optical signal generated by optically active media in the resonator 150 particularly a microresonator, and/or an optical process mediated by or originating from an analyte and/or perturbative member 100. However, embodiments disclosed herein are not limited to overcoupled bus/waveguide geometries.

Figure 5:

FIG. 5 shows a waveguide 150 in the form of a resonator, for example a disc, toroid, ring, ellipsoid, and/or sphere. A bus waveguide 170 can couple an electromagnetic wave into and out of the resonator. The bus waveguide may lead to a coupler, particularly input/output couplers which may couple free space electromagnetic energy to/from waveguided EM waves in the bus, such as a grating coupler. A light source such as a laser is not shown, which can be operably coupled to the bus waveguide, such as through an input coupler. Similarly, a detector can be operatively coupled to the bus waveguide. A perturbative member 100 is shown which can perturb the electromagnetic modes supported by the resonator. A gap 120 is disposed between the nearest surface of the waveguide 150 and the perturbative member 100, and is also disposed so as to perturb an electromagnetic wave with a portion of the mode near the perturbative member between the waveguide 150 and the bus waveguide 170. This disposition of the perturbative member can perturb and/or modulate the coupling strength of the bus and resonator, and may be particularly sensitive to binding of an analyte to the perturbative member or the vicinity of the perturbative member.

Figure 6:
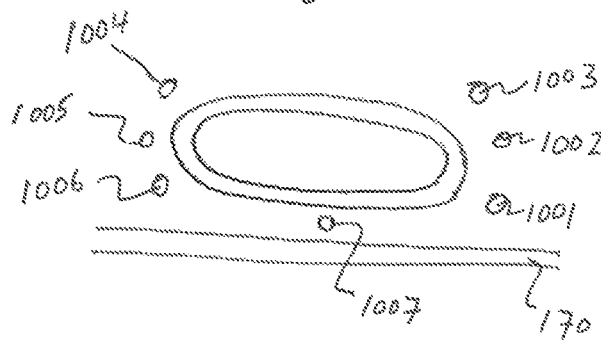

FIG. 6 shows a waveguide assembly in the form of a racetrack resonator 1501 and a bus waveguide 170. Several possible positions of at least one perturbative member are shown, 1001 through 1007. A perturbative member may be at exactly one of the positions, or at least one of the positions, including a plurality of positions. A waveguide assembly, particularly including a microresonator, with more than one perturbative member is contemplated (including embodiments which include microresonators 1501 other than racetrack resonators). A plurality of perturbative members which are operatively coupled to a microresonator may advantageously bring about sensitivity of the resonator modes to each of the perturbative members individually and/or collectively. For example, a microresonator electromagnetic mode may be modulated and/or perturbed by more than one perturbative member, and/or be perturbed by analytes which may bind to the perturbative members.

An advantage of having perturbative member(s) located near curved regions of the resonator 1501 is that the mode volume of an electromagnetic wave supported by the waveguide may have more density at curved positions in comparison to straight positions. Therefore, the electromagnetic mode may be more sensitive to the perturbative member or their respective vicinities. Embodiments which include more than one perturbative member are not limited to racetrack resonators; other waveguide assembly forms, particularly other resonator types (disc, sphere, etc) are contemplated.

Figure 7:
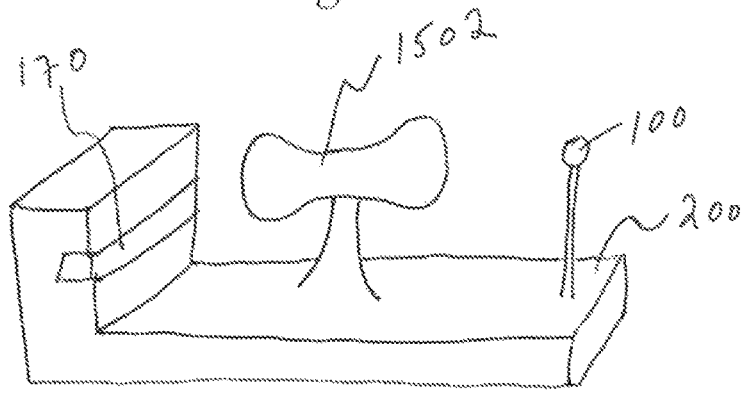

FIG. 7 shows a waveguide assembly in the form of a resonator 1502 in the form of a toroidal resonator, although disc resonators and other shapes are also contemplated. A bus waveguide 170 can couple to the resonator 1502. A perturbative member 100 can perturb an electromagnetic wave supported by the resonator. A support 200 is also shown which can support the resonator, waveguide, and/or perturbative member.

FIG. 8 is similar to FIG. 7 and shows a form of a bus waveguide 170, which can be an optical fiber such as a tapered optical fiber, which can be disposed on the support 200 such as directly on the support.

FIG. 9 is similar to FIGS. 7 and 8. Whereas as shown in FIGS. 7 and 8, the support 200 may support the resonator 1501 and the perturbative member 100, in FIG. 9 a second support 210 may support the perturbative member 100. The second support may include an actuator, e.g. a piezoelectric transducer, for adjusting the position of the perturbative member, particularly with respect to the microresonator, such as after the second support is fixed to the first support. It may be advantageous to ensure that any metal components (such as metal electrodes, if present) of the actuator are located significantly farther from the microresonator than the perturbative member. This may reduce perturbations on the microresonator by the metal parts of the actuator. Significantly farther may mean from at least about 0.5, 1, 2, 5, or 10 micrometers away from the nearest surface of the resonator and/or the perturbative member. It can be possible to have metal parts of the actuator located more than a millimeter away from the perturbative member and/or resonator. For example, for longer wavelength applications (a resonator mode of longer wavelength), due to an increase in the extent of the evanescent field, a farther distance from the resonator to the perturbative member can result in desirable perturbations of the perturbative member on the electromagnetic modes of the resonator. Similarly, for applications employing longer wavelength electromagnetic modes that may be supported by the resonator, the metal components of the actuator, if present, may be at a greater minimum distance to the resonator to reduce unwanted perturbations of the electromagnetic modes of the resonator by any metal components of the actuator.

Furthermore, perturbative members may be metal or semiconductor nanowires of up to about 100 micrometers in length, and may support plasmon resonances. One end of the nanowire may be located near a surface of the microresonator, whereas the other end may be directed radially outwardly, or in the same direction as the symmetry axis of the resonator. Alternatively, an inner part of the nanowire (not either of its ends) may be closest to the resonator. The length of the nanowire, particularly that of metal nanowires, may be tuned so as to support a plasmon resonance that can be in relation to an electromagnetic mode supported by the resonator, such as in resonance with an electromagnetic mode of the microresonator. The plasmon resonance and EM mode of the microresonator may be co-resonant. In some embodiments, the perturbative member may be movable, such as having a mechanical resonance or being actuatable, and the movement of the perturbative member may shift the resonant EM mode of the microresonator. In such a case, the plasmon resonance of the perturbative member may be co-resonant with an EM mode of the microresonator at at least one position. The position of the perturbative member can alternatively/additionally tune the supported EM resonance of the microresonator.

FIG. 10 shows a waveguide assembly 150 in the form of a resonator with an angled region 155 which is disposed near the perturbative member 100. The angled region 155 and nearby perturbative member 100 may serve to increase the fraction of the electromagnetic mode which can be perturbed by the perturbative member, for example by increasing the modal energy of a electromagnetic wave in the vicinity of the perturbative member (e.g. in the evanescent region).

FIG. 10B shows a resonator 150 with a perturbative member 100 having a long axis, e.g. a nanowire. The long axis (nanowire) can oriented to make an angle 310 of approximately 130 degrees with a surface of the microresonator 150. An angle 310 of approximately 130 degrees can have greater electromagnetic coupling between the resonator 150 and an elongate perturbative member 100 (i.e. a perturbative member with a long axis such as a nanowire). It is mentioned that an array of metal particles (at least two), or a metal coating or film, may serve as a perturbative member with a long axis. It is also contemplated that an angle of from about 120 to about 140 may also be the angle 310. It is further contemplated that the value of 130 degrees is based on a reasonable angle of maximum free space optical radiation emission from a plasmon polariton supported by a nanowire, and because the resonator 150 has a higher index of refraction than air which may support coupling of the electromagnetic wave, this may alter the coupling angle for maximum coupling, particularly increase it. An angle of maximal coupling can be estimated and/or predicted using modeling techniques such as Greens functions and the like to predetermine an optimal angle between a nanowire (e.g. of a given composition) and a surface of the resonator. It is possible to determine a device geometry which maximizes optical coupling between a plasmon supported by a nanowire and a microresonator. It can be desirable to have the plasmon mode(s) from the nanowire at a position at which generated photons (from the end of the nanowire directed toward the microresonator) are directed along the path of the electromagnetic waves supported by the microresonator, e.g. whispering gallery mode resonances. Adjustable parameters are for example the distance between the nanowire and the microresonator, the width of the nanowire, the gap between the end of the nanowire and the microresonator, and the angle between the nanowire and a surface of the microresonator. In this case, "surface of the microresonator" can be a surface adjoining a region of the microresonator surface of maximal curvature, and which may be substantially or completely linear in cross-section (in the cross-sectional plane bisecting the resonant electromagnetic mode of the resonator) over a distance of approximately a quarter wavelength 0.25λ, half a wavelength (0.5λ) or greater such as λ, 2λ, 3λ, 4λ, or 5λ. The angle made by this linear section of the resonator and the nanowire may be predetermined such as by theoretical modeling, theoretical prediction validation and/or refinement by experimental methods such as measuring coupling efficiency, and trial and error experimentation to, for example, increase coupling efficiency.

FIG. 11 shows a waveguide assembly 150 in the form of a resonator with region 300 near the perturbative member which includes an optically active media, e.g. $Nd^{+3}$, $Y^{+3}$, $Er^{3}$, $Th^{+3}$, $Ho^{+3}$, $Pr^{+3}$, a gain media such as a rare earth dopant (for example Eu ions, rare earths, and/or laser dyes). Particularly, the region 300 with the optically active media has the optically active media in a concentration greater than at regions farther from the perturbative member 100. (This region 300 may also be more curved than other regions, and/or have a cusp, notch, or angular projection). The resonator may be otherwise passive, such as having no optically active medium other than near the perturbative member; or the resonator can have elsewhere a lower concentration of the optically active media. In another example, the optically active medium is present at a lower concentration in the region 300 in comparison to other regions of the microresonator 150, for example, the concentration of the optically active medium in other regions is sufficient for self-quenching to be significant.

Alternatively or additionally, the resonator can have more than one kind of optically active media, for example a first kind disposed near the perturbative member, and a second kind disposed elsewhere in the resonator. An effect of having an optically active media at greater concentration disposed near the perturbative member is to increase the sensitivity of an optical signal arising from the optically active media to the perturbative member, such as fluctuations of the position of the perturbative member, and or binding of an analyte to the perturbative member such as in the evanescent region near the perturbative member.

Asymmetric distribution of optically active media in and/or on the resonator can for example be facilitated by precision drop casting materials such as sol-gel materials, colloidally dispersed doped silica particles, and optional annealing. Microcapillaries, e.g. with nanometric actuators and positional feedback capabilities, while observation is made by microscopic means, can be used to deliver precise small volumes of solvated optically active media, precise in both location where the delivery is made and in volume of the deliver. Ion implantation may also be used.

The microresonator can include an optically active media disposed asymmetrically such that a greater or lesser concentration of an optically active media is in a region near the perturbative member in comparison to a region farther from the perturbative member. For example, the region of the microresonator near the perturbative member can have a greater or lesser concentration of the optically active media in comparison to the average concentration of the optically active media of the (remainder of the) perturbative member.

It is further contemplated herein to have a perturbative member in contact with a resonator surface (which may optionally include a coating); a locally higher concentration of an optically active media in the resonator, near the perturbative member, can lead to more sensitive optical signals arising from the optically active media which are perturbed by the perturbative member. For example, binding of an analyte to the perturbative member can alter the local index of refraction, alter the electromagnetic wave path, and/or electromagnetic resonant pathlength. Particularly, for example, when the region of the resonator near the perturbative member includes a locally higher concentration than elsewhere of an optically active media such as a lasing media, the intensity of signal such as lasing from the optically active media can be highly sensitive to the presence of an analyte. It is furthermore contemplated that the perturbative member can move such as oscillate so that it makes intermittent and/or periodic contact with the resonator. For example, a pulsed electromagnetic wave supported by the resonator may induce movement of the perturbative member. Furthermore, it is possible that an amplitude modulated EM wave may thus induce mechanical motion such as resonant mechanical motion of the perturbative member. Alternatively or additionally, a weak or lack of an electromagnetic wave supported by the resonator may allow the perturbative member to be located at a gap distance from the resonator, whereas a more energetic electromagnetic wave supported by the resonator may decrease the gap distance and/or cause contact of the perturbative member with the resonator.

FIG. 12 shows a waveguide assembly including a waveguide 150 in ring form, and a perturbative member 100 located inside the ring. Thus, in addition to waveguide assemblies which include a resonator and a perturbative member(s) located radially outwardly from the resonator, it is also contemplated to dispose the perturbative member(s) radially inwardly from the resonator. This is also possible with racetrack resonators. For disc resonators, perturbative members can be outwardly or inwardly disposed also, although, for example, in the case of disc resonators the perturbative member can be to be located some distance along the axis of symmetry of the disc, as shown in FIGS. 13 and 14. It is possible that a plurality of perturbative members are disposed, at least one radially outwardly and others radially inwardly of the resonator, or a plurality of perturbative members may be located exclusively inwardly or outwardly.

FIG. 15 shows how separate components of a waveguide assembly can be constructed individually and fixed together. For example, the bus, resonator, and perturbative members can each be made on separate substrates, and the substrates assembled in a desired geometry. For example, bus piece 270 includes a support 177 and the bus waveguide 170. The resonator assembly 370 includes a resonator 1501 and support 200. The perturbative assembly includes the perturbative member 100 and a support 210. The bus 170 and resonator 370 can optionally be coplanar, particularly for disc, toroidal, or ring resonator, or the bus may coincide with a center plane of a spherical resonator. The perturbative member can be optionally coplanar with the resonator. It is also contemplated to construct some or all of the components monolithically for example on the same substrate, such as a silicon substrate or "silicon on insulator."

Materials such as silicon, silica, silicon nitride, silicon oxynitride, silicone, metals, metal oxides, germanium, polymers (e.g. SU-8, PMMA), and the like, such as materials used in microdevices and/or fabrication of microdevices can be employed to form many of the structures described herein, particularly supports, waveguides, and/or microresonators.

Components can be assembled by the use of actuators such as piezoelectric actuators, optical traps, electrophoretic and/or dielectrophoretic traps (cages), etc. Further possible materials are metals particularly noble metals, particularly in the perturbative member, and can be in the shape of (nano-) rods, wires, stars, and/or oxide coated wires. Semiconductor nanowires are also contemplated for use as perturbative members.

Adhesives such as epoxies, silanes, polymers (e.g. SU-8), and the like can be used to fix components together, particularly slab shaped components which support other components, which can optionally make the use of surface functionalized faces of components. Etching, deep reactive ion etching, etching with $XeF_2$, etching with HF including buffered HF, KOH etching, acid etching, ozone treatment for example for cleaning, lithography, photopolymerization (e.g. 2 photon polymerization), polymerization, ion beam milling, electron beam lithography, micromachining, isotropic and/or anisotropic etching, physical vapor deposition, chemical vapor deposition, molecular beam epitaxy, plasma etching, inductively coupled plasma reactive ion etching, vapor-liquid-solid nanowire growth, polymer grafting, chemical functionalization such as by the use of click-chemistry and/or conjugation, biotin-streptavidin and other noncovalent binding interactions such as immunochemical pairs, covalent binding, oligonucleotide binding, DNA origami methods, silanization, growth of thin films such as oxide films, the use of lithography masks such as negative and/or positive photoresist (e.g. PMMA, hydrogen silsequioxane), wafer bonding (e.g. adhesive bonding, plasma-activated bonding, reactive bonding, and direct bonding), sputtering for example magnetron sputtering, electroplating, electroless plating, electrochemical deposition, cleaning for example with UV, ozone, and/or supercritical $CO_2$, $SiO_x$ overlayer formation by for example plasma enhanced CVD with silane and $N_2O$, inkjet printing such as noncontact inkjet printing, stamping, spotting, scanning probe lithography, AFM manipulation, optical tweezers, and the like can be used to form and/or assemble components.

The perturbative member may include a dielectric particle, metal particle, or combination thereof, and may further include or be attached to a binding site/region which may bind an analyte (e.g. the binding site/region is (part of) a single strand of DNA and the analyte is a complementary or at least partially complementary single strand DNA). Alternatively or additionally, the perturbative member may include a structure for providing a restoring force that may oppose a force attracting the perturbative member toward the waveguide, such an attractive force arising for example due to a field gradient. Structures which may act as the perturbative member or support a perturbative member, such as cantilevers, double or single beams of micromachined materials such as silicon, silica, silicon nitride, polymers, and piezoelectric materials, for example, are contemplated.

The perturbative member can perturb the electromagnetic wave passing through (supported in) the waveguide. For example, due to the field gradient the perturbative member can experience an attractive force toward the waveguide, which may displace the perturbative member. The displacement of the perturbative member in turn may for example increase scattering and/or absorption of electromagnetic energy, and reduce throughput of electromagnetic energy; alternatively or additionally the displacement of the perturbative member may perturb the effective refractive index of the evanescent region. The perturbative member may also cause splitting of a supported EM mode of a nearby resonator.

Alternatively or additionally, if the perturbative member includes a binding site/region, the binding of an analyte to the binding site if the perturbative member may perturb the effective refractive index of the evanescent region. Particularly if the waveguide is part of a microresonator, binding of an analyte may cause a shift and/or mode splitting of an electromagnetic resonance mode of the microresonator.

An advantage of the location of the perturbative member being beyond the waveguide assembly, and/or away from a nearest surface of the waveguide (e.g. such that there is a gap between the waveguide assembly and the perturbative member) is that the binding site/region does not affect the surface roughness of the waveguide assembly. For example if the waveguide assembly is part of a microresonator, the presence of the perturbing member has less of a deleterious effect on the quality factor (Q) of the microresonator; alternatively or additionally, there can be a decreased probability of irreversible adsorption of the analyte on the waveguide assembly; for example a binding site/region that is not on the surface of the waveguide assembly but located away from its surface, i.e. on the perturbative member or near it, is less likely to result in fouling of the microresonator surface by an analyte particularly if the microresonator surface is coated with an antifouling agent such as a coating to resist nonspecific binding.

FIG. 16 shows a perturbative member 100 which includes a structure 400 providing a restoring force to oppose the attractive force toward the resonator 1501. In the case of a very stiff structure 400, there is little or no displacement of the perturbative member, thus there is little or no detectable perturbation of the electromagnetic wave; however if the perturbative member includes a binding site/region, there may be detectable perturbation of the electromagnetic wave for example by perturbing the effective refractive index of the evanescent region, even if the position of the perturbative member 100 is not influenced by the presence of an electromagnetic wave travelling through the resonator 1501.

FIG. 17 shows a perturbative member 1001 having a long axis. For example, the perturbative member with a long axis can include a metal (e.g. Al, Ni, Ti) such as a noble metal like Ag, Au, and their respective alloys, or a semiconductor nanowire or nanorod. The perturbative member, nanowire, and/or nanorod can be coated with a dielectric substance such as silica, a surface passivation agent, and/or a coating to resist nonspecific binding of components of an analyte. A coating may allow for protecting the surface from contamination or may stabilize it from oxidation or the effects of heating. A coating may allow for spacing the nanorod or nanowire from other components such as the surface of a waveguide and/or microresonator. A coating may also allow for chemical modification of the nanowire or nanorod, for example to facilitate the attachment of a binding site/region to the nanorod or nanowire. A coating can be provided on a perturbative member even for cases where the perturbative member is shaped other than a nanowire or nanorod. Coatings such as for example silica, polymers, silanes, and organothiols are contemplated.

A metal, particularly a noble metal with a long axis can support plasmons and/or plasmon polaritons, can enhance the electric field near the perturbative member, and/or alter the optical properties of the environment such as alter the path of an electromagnetic field travelling in the waveguide or microresonator.

FIG. 18 shows a microresonator 150 which has a more curved region directed toward and/or in the vicinity of a perturbative member 100 in the shape of a nanowire. The local curvature, near the perturbative member, is greater than the curvature of the microresonator elsewhere. In other words, the nearest surface of the microresonator to the perturbative member is curved with a curvature greater than a farther surface of the microresonator. Such a geometry can increase the mode volume of an electromagnetic mode in the region near the gap between the resonator 150 and the nearest end of the nanowire 100. A more curved region directed toward a perturbative member is also contemplated in embodiments other than those having a nanowire shaped perturbative member. Adjacent to the more curved region can optionally be a linear region, as depicted.

FIG. 19 shows a silica disc resonator 150 on a silicon substrate which has a ledge 220. A ledge, slot or the like may be useful in aligning a second support which supports the perturbative member to the resonator 150.

FIG. 20 shows a simple structure for facilitating the modular placement of an actuable perturbative member near a microresonator supported on a substrate. An actuator 500 such as a piezoelectric actuator is bonded to a support piece 510 such as a dielectric such as alumina, silica, silicon nitride or the like. A sacrificial piece 520, for example made of a soluble polymer or selectively etchable material, can be disposed on the support piece 510. In FIG. 21 a nanowire 555 is placed across the interface between the sacrificial piece 520 and the support piece 510, and fixed to the support piece 510. For example, a drop of solution of TEOS may fix a silica coated silver nanowire to a silica support piece 510; the drop can be placed on the wire and support piece. The sacrificial piece can be removed such that the nanowire protrudes from the end of the support piece 510, as shown in FIG. 22. It is noted that the structure resembles a cantilever, and cantilevers such as those commonly used in atomic force microscopy and related technologies, are also contemplated for use in actuated or non-actuated supports for perturbative members. An actuable (movable) perturbative member may have a direction of actuable motion toward or away from the resonator surface, or any other direction, such as perpendicular to it, and/or may rotate.

FIG. 22B shows an embodiment in which the support piece 510 leaves a gap, and is not flush with the bottom surface of the actuator. This is advantageous for control of the motion of the perturbative member. The actuator can be a linear, rotatable, and/or shear actuator, etc. The actuator can adjust the gap distance, for example.

FIG. 23 shows an embodiment in which a bus waveguide 170 is buried under the resonator 150. The nanowire 555 serves as an actuable perturbative member. Placement of the perturbative member assembly (500, 510, 555) on the support 200, can be facilitated by careful pre-measurement and observation of feducial marks (not shown) on the support piece 510 and base 200, particularly before and during assembly. Alternatively or additionally, a measurement of light intensity from the far end of the nanowire (the end farther from the resonator) can be monitored as the perturbative member assembly is approached to the resonator which is supporting an electromagnetic wave which will couple to the perturbative member when it is close enough. Alternatively or additionally, the perturbative member may be oscillated by an oscillating driving force provided by the actuator 500, and the optical signal (e.g. the output of the bus waveguide) may be monitored at the oscillation frequency (the natural frequency) of the perturbative member's mechanical resonance.

Structures such as a resonator 150 can be fabricated by use of a photolithographic mask on a silicon wafer that has been oxidized to provide a silica surface, etching, and so on. A silica coated nanowire 222 such as a silica coated silver nanowire 222 can be placed at a desired geometry on a surface for example by use of dielectrophoretic traps can, and/or optical tweezers, and or mechanical methods for example using a scanning and manipulating probe such as is common in scanning probe methods. For example, a nanowire can be provided colloidally, and be gripped and manipulated by optical tweezers. Gripping and manipulating nanowires can be by for example by methods described by Yan et. al in Nano Letters (Controlling the Position and Orientation of Single Silver Nanowires on a Surface Using Structured Optical Fields. Zijie Yan, Julian Sweet, Justin E. Jureller, Mason J. Guffey, Matthew Pelton, and Norbert F. Scherer. ACS Nano, 2012, 6 (9), pp 8144-8155), or for example a time-shared optical tweezers which provides two horizontally displaced focal points.

Figure 24:
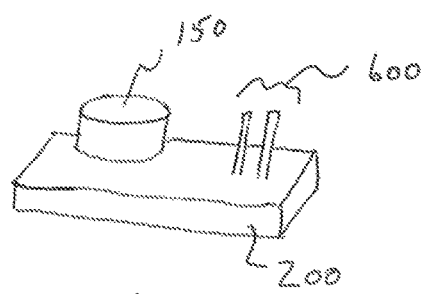
FIGS. 24, 25, 26, 27, and 28 shows a resonator, each according to embodiments described herein.

FIG. 24 shows a resonator 150 and two posts 600, although one or more posts are also contemplated. Posts can be used to aid placement and/or attachment of the perturbative member, particularly perturbative members supported by polymer filaments such as DNA strands.

Figure 25:
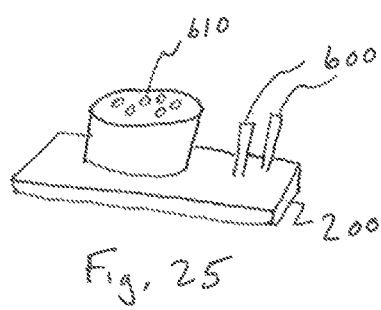

FIG. 25 shows the structure of FIG. 24 with (optical) handles 610 such as micrometer particles made of for example polystyrene and silica, disposed on the surface of the resonator 150. The (optical) handles can be drop coated from a colloidal suspension using precision microcapillary techniques. The handles 610 can be functionalized with a sticky-ended polymer strand such as an oligonucleotide such as DNA, e.g. with an end-functional group amenable to attachment with the resonator (e.g. has been attached to the resonator). For example, one end of the single stranded DNA is attached to the handle 610 and the other is configured to be attachable to the center portion of the resonator, which may itself be functionalized, e.g. spatially selectively, to allow attachment of the DNA).

Herein, "optical handles" can refer to structures that can be manipulated using optical tweezers and/or electrophoretic techniques, and/or dielectrophoretic techniques. For example, they include chemical species on their surface which are amenable to attachment to other surfaces, and can be colloidally dispersed.

Figure 26:
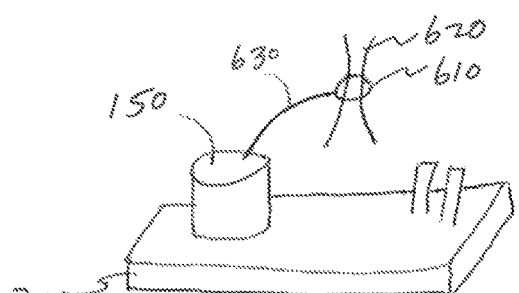

FIG. 26 shows an optical handle 610 being manipulated by optical tweezers. Dispersion of the handle(s) in a media can be aided by using a solvent such as water, and the optical tweezers may be facilitated by a suitable microscope, optics, etc. The handle 610 can be moved so that the polymer strand 630, e.g. DNA extends radially outwardly from the microresonator. The handle can be fixed to the substrate 200 and/or a post(s) 610 or other feature extending from or attached to the substrate support 200. Alternatively or additionally, dielectrophoretic forces can be used to stretch the polymer strand, e.g. by the use of positionable electrodes. The polymer strand may include a binding site/region for attachment of an analyte, and may further include a nanoparticle such as a metal nanoparticle, particularly near the binding site, so as to increase the electromagnetic field intensity in the vicinity of the binding site. Optionally, the nanoparticle may serve as the perturbative member. The binding site for attachment of an analyte may be situated so as to be between the nanoparticle and the resonator, or the nanoparticle may be between the resonator and the adhering site of the optical handle 610 which can be fixed (after stretching the polymer strand for example) to the posts 600 and/or substrate 200.

Figure 27:
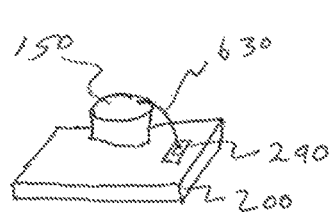

FIG. 27 shows a microresonator 150 on a support 200, the support having an adhesive region 290 for tethering an end of the polymer strand 630. For example the adhesive region can be a surface functionalized region of the support 200, which may cover the support, or cover part of the support. The adhesive region 290 may lie at a distance from the edge and/or center of the waveguide 150. The adhesive region may covalently or noncovalently bond to the polymer strand 630 and/or optical handle which is attached to the polymer strand. The polymer strand may be tethered to an edge of the resonator or a central portion of the resonator. A binding region/site of the polymer strand, which can be coded to bind to an analyte, may lie at a position so as it is disposed away from the surface of the resonator, for example the binding site/region is away from the surface of the resonator by at least about 1 nm, or 2 nm, 3 nm, 4 nm, 5 nm, 6, 7, 8, 9, or 10 nm, or 12, 14, 16, 18, or 20 nm, or 25, 30, 35, 40, 45, 50 55, 60, or 70, 80, 90, 100, 120, 140, 160, 180, 200, or from 200 to 500 nm, or 500 to 1000 nm. Lower values of the distance may provide greater sensitivity of the resonator's optical modes for example on the presence of an analyte that may bind to the binding region/site, particularly less than about 50 nm. It is noted that the distance may be adjustable, for example by increasing/decreasing the electromagnetic energy in the waveguide/resonator 150. Greater energy in the resonator, for example, may increase the optical gradient force so as to reduce the distance and may increase the tension in the polymer strand. For example, pulsing of the intensity of an electromagnetic wave through a bus waveguide coupled to the resonator may cause oscillations of the position of the binding site and/or oscillations of tension of the polymer strand.

Binding of the polymer strand can be facilitated by the use of end-functionalized polymer strands for example, and may be through the use of click chemistry, selective agents for interstrand and/or intrastrand covalent coupling of DNA, photochemically reactive species, conjugation chemistry agents, and the like. An adhesive region 290 can be prepared by lithography, for example dip pen lithography, photolithography, etc.

Figure 28:
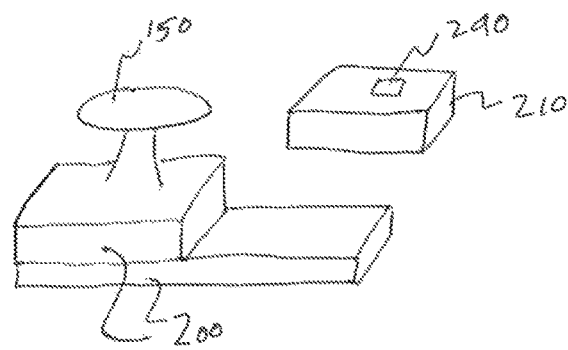

FIG. 28 shows a waveguide 150 on a support 200, and an adhesive region 290 on a second support 210 that can be adhered to the support 200. Optionally, the entire block or top surface of the second support 210 can serve as an adhesive region. Furthermore optionally, the second support 210 can have a waveguide and/or optical resonator which can be used to provide an optical gradient force to attract an optical handle toward a binding region, and furthermore optionally provide a light source for photopolymerization to bind the optical handle to the adhesive region 290. Alternatively or additionally, the second support can have electrodes for providing a (di-)electrophoretic force for positioning the optical handle. For example, the optical handle ((di-)electrophoretic handle) can be attracted to an electrode or gap between electrodes.

Figure 29:
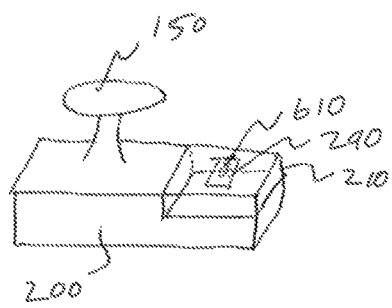
FIGS. 29 and 30 show a waveguide on a support and an optical handle, each according to embodiments described herein.

FIG. 29 shows an optical handle 610 on an adhesive region 290, the adhesive region 290 covalently bound to one end of a polymer strand 630 (seen in FIG. 30), and another end of the polymer bound to the optical handle 610. Optionally, the optical handle and adhesive region are prepared on a second support 210 which is subsequently attached to the support 200. The optical handle 610 can be attracted to and bound to the surface of the resonator 150 by the optical gradient force of for example a whispering gallery mode supported by the resonator 150, the electromagnetic wave provided for example by a bus waveguide coupled to the resonator 150.

Figure 30:
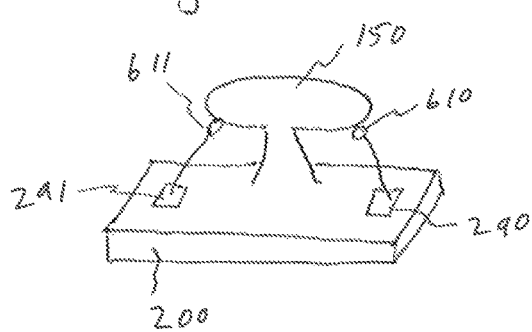

FIG. 30 shows the polymer strand 630 attached to the waveguide/resonator 150 through the optical handle 610. Optionally, there are a plurality of polymer strands attached to the waveguide. For example, as shown, there is a second polymer strand 631 and second optical handle 611. Silica based optical handles may be advantageous, since they may attach through siloxane bonds to a silica waveguide 150, although surface functionalized optical handles and/or surface functionalized waveguide assemblies may broaden possible materials. Core-shell optical handles are also contemplated, for example a gold core@silica shell may be heated by the electromagnetic field to strengthen the adhesion of the optical handle 610 to the waveguide 150. Attachment can also be facilitated by adding a small amount of TEOS and optional catalyst such as ammonia to a solution during attachment (e.g. while energizing the resonator with an electromagnetic wave to provide the optical gradient force).

It can be possible to arrange the optical handle(s) 610 disposed on the adhesive region(s) 290 so that the optical gradient force results in attachment of the handle to the resonator 150 rather than the bus waveguide, e.g. the bus can be disposed on the opposite site of the adhesive region 290.

It is also contemplated that perturbative members that include metal such as a metal nanoparticle or metal film may not necessarily be tuned such that the plasmon supported by the perturbative member is resonant with a supported whispering gallery mode of the resonator. A nearby plasmon resonant perturbative member may decrease Q of the resonator. Maintaining a high Q can be desirable for some applications. On the other hand, there are applications which may benefit from greater coupling between the perturbative member and the resonator, which may be increased by tuning the supported plasmon mode of the perturbative member to the resonator, or vice versa. Also, the breadth and/or density of plasmon modes of a perturbative member may be rather large, particularly in comparison to a single whispering gallery mode of a nearby resonator. For example, the resonator may support a mode near on an edge of a plasmon mode of the perturbative member. Furthermore, actuable perturbative members may have variable plasmon resonances. For example, consider a perturbative member that includes a metal particle disposed near the resonator, or near a dielectric such as a dielectric surface of the waveguide assembly/resonator and/or a separate dielectric particle or structure: if the distance between the dielectric and the metal is variable, e.g. oscillates, the plasmon resonance can shift depending on this distance, thus giving possibility of having a variable plasmon resonance (e.g. tunable or modulateable). Variable plasmon coupling to the resonator is further contemplated by for example a mechanical actuator such as a piezo (moving the perturbative member and/or an additional nearby dielectric or metallic (or combination) species).

Figure 31:
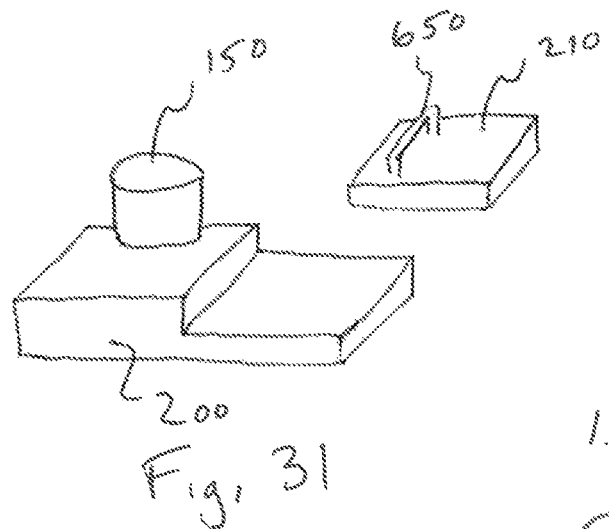
FIGS. 31, 32, and 33 show a resonator on a substrate and a mechanical resonator, according to embodiments described herein.
Figure 32:
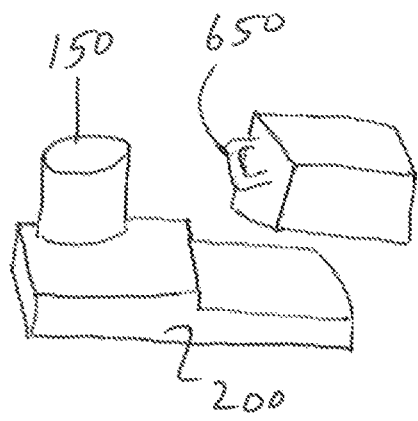
Figure 33:
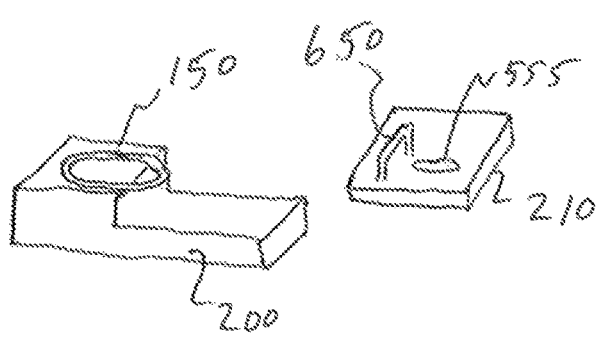

FIG. 31 shows a resonator 150 on a substrate 200, and a second substrate 210 which supports a mechanical resonator 650 such as one formed as a silicon nitride beam which may be fixed at one or both ends. The second substrate 210 can be attached to the first substrate 200 (e.g. to couple the (electromagnetic) resonator 150 and the mechanical resonator 650), or the mechanical resonator 650 can be formed on the same substrate as the resonator 150. FIG. 32 shows an alternative geometry. The principle flexing direction of the mechanical oscillated can be parallel or perpendicular to a polarization direction of a supported electromagnetic mode of the resonator, or may be at an angle to it. A mechanical oscillator may serve as a perturbative member or a component of a perturbative member. A mechanical oscillator may also have a metal coating or metal particle attached to it, for example to increase field strength near the mechanical oscillator. FIG. 33 shows a microresonator 150 on a substrate 200, and a second substrate 210 supporting a mechanical resonator 650 and nearby metal structure which may be a nanowire 555. For example, when the second substrate 210 is attached to the first substrate 200, a portion of the metal structure 555 and/or mechanical resonator 650 can lie beneath the microresonator, for the mechanical resonator 650 is configured to modulate the coupling between an electromagnetic mode supported by the microresonator 150 and the structure 555 which can include a metal nanowire, a dielectric-coated metal nanowire such as silica coated silver, or a semiconductor—metal complex such as a VLS grown nanowire, particularly such that the end of the wire is either a semiconductor or metal, and the body of the wire is, respectively, a metal or semiconductor.

There may be an advantage of having a mechanical oscillator, for example as part of a perturbative member, which is near a binding region for an analyte, particularly such that an electromagnetic wave supported by the waveguide and/or resonator can be perturbed by both the analyte and the mechanical oscillator. The mechanical oscillator may provide a reference frequency and/or modulation frequency at which the sensitivity of detection of the analyte is increased.

Mechanical, such as spatially varying, oscillations of the perturbative member can be fundamental mechanical oscillatory modes of the perturbative member. The mechanical oscillations can have a fundamental mode in a direction predominantly tangential to the nearest surface of the resonator and/or a fundamental mode in direction predominantly perpendicular to the nearest surface of the resonator. The fundamental frequency or frequencies of the mechanical mode(s) of the perturbative member can be influenced by the shape of an actuator and/or supporting structure for the perturbative member, for example. There may be two, or more, nondegenerate fundamental mechanical modes of the perturbative member. For example, there is a fundamental mode which is a mechanical oscillation of the perturbative member substantially perpendicular to the direction of the travelling EM wave supported by the waveguide, at the nearest surface of the resonator, and a second fundamental mode which is substantially parallel to the direction of the travelling EM wave at the nearest surface of the resonator. The second fundamental mode may be nondegenerate with the first. Nondegeneracy of fundamental mechanical modes of the perturbative member may be realized by forming perturbative members, and/or support structures for the perturbative member which are not symmetric. For example, the perturbative member 100 is supported by a mechanical oscillator 650 (or the perturbative member 100 is the mechanical oscillator 650) in the shape of a rectangular beam (see for example FIGS. 31 and 32). The faces of the beam can be parallel to and perpendicular to the direction of the travelling EM wave supported by the waveguide, at the nearest surface of the resonator.

Figure 34:
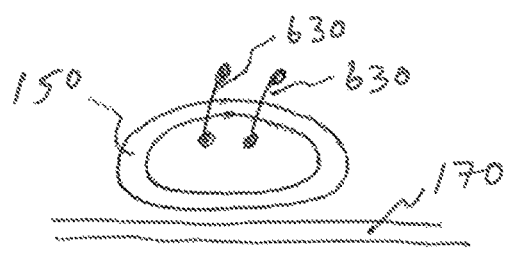
FIGS. 34 and 35 show a polymer strand disposed over a waveguide, each according to embodiments described herein.
Figure 35:
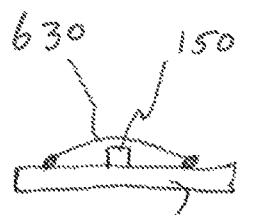

FIGS. 34 and 35 show two views of a polymer strand 630 disposed over a waveguide 150, which can be part of a microresonator for example a ring or racetrack resonator. A bus waveguide 170 is shown in FIG. 34. FIG. 35 shows a cross-section of the waveguide 150 supported on a substrate 200. The polymer strand 630 can include a region such as a binding region which is suspended away from the surface of the waveguide 150 and the support 200. Particularly in the case that a binding region/site is disposed on or is part of the polymer strand, an analyte, which desirably binds to the binding region/site, has reduced nonspecific binding interactions with the waveguide 150, particularly if the waveguide is coated with a nonspecific binding reduction agent (e.g. PEG). The polymer strand can be attached, optionally through an optical handle, to the substrate 200 such as a surface functionalized substrate, or a region of the substrate which has been surface-functionalized.

Figure 36:
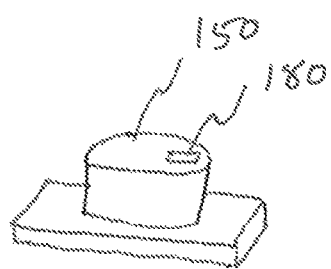
FIG. 36 shows a resonator with an elongated perturbative structure, according to embodiments described herein.

FIG. 36 shows a resonator 150 with an elongated EM perturbative structure 180 such as a strip and/or nanowire. A metal strip may be a thin metal strip oriented with its long axis having a component of its long axis pointing away from the center of the resonator. A nanowire such as a metal nanowire or oxide nanowire may be positioned similarly. An EM perturbative structure 180 may reduce the Q of the resonator 150. An EM perturbative structure 180 may provide a locally enhanced region of an electromagnetic wave supported by the resonator, such as to direct the attraction and/or attachment of an optical handle and/or perturbative member 100. An elongated EM perturbative structure 180 may be embedded in the resonator, for example by application of an overcoat of an oxide by using TEOS or SiO$_x$ deposition. A plurality of elongated EM perturbative structures 180 are contemplated, for example to enable multiple positions of local enhancement and/or to facilitate attachment of multiple optical handles, and/or provide attraction to nearby perturbative members. The EM perturbative structure 180 can be combined with a perturbative member 100 located at a gap distance from the surface of the microresonator 150. For example, the perturbative structure 180 is aligned with a perturbative member 100. For example, the nearest edge face and/or nearest surface of the microresonator to an end of the perturbative structure 180 is also the nearest surface of the microresonator 150 to the perturbative member 100.

Figure 37:
FIG. 37 shows a resonator with a region of smaller radius of curvature, according to embodiments described herein.

FIG. 37 shows a microresonator 150 having a region 152 having a smaller radius of curvature than the rest of the resonator. Such asymmetry may reduce Q and may also serve to increase the local electric field of the resonator, particularly an evanescent field. For example the increased local electric field can be used to attract a perturbative member and or optical handle. It is also possible that the local deformity 152 is the result of attachment and optional annealing (particularly for the case of a silica optical handle) of an optical handle to the resonator.

For example an optical handle is held by an optical trap provided by a focused light beam in the vicinity of a resonator, such as a symmetric resonator lacking a region 152. The light can be focused at a position radially outwardly and in the plane of the top surface of the resonator. Next, a supported mode of the resonator is turned on by introduction of an EM wave through a bus waveguide. Optionally, a small displacement of the optical handle is determined, the displacement being toward the resonator (e.g. a change in the scattering by the optical handle can be determined). The optical trap is turned off, for example by blocking a laser beam which is providing the gradient force of the optical trap. The handle is then attracted to the microresonator, and the applied EM field in the bus is blocked, optionally after a time period for heating via the EM field supported by the resonator to drive covalent attachment of the handle to the resonator. For example, this can be done in a solution, for example a solution including a chemical linker to link the handle to the resonator, for example TEOS (tetraethylorthosilane) and ammonia. Other covalent attachment schemes are possible. The optical handle can include an optically active media for example dispersed in a silica or polystyrene handle, a metal core such as a metal nanoparticle (e.g. gold and/or silver). Alternatively or additionally, the optical handle can be a core/shell particle with metal on the outside.

Figure 38:
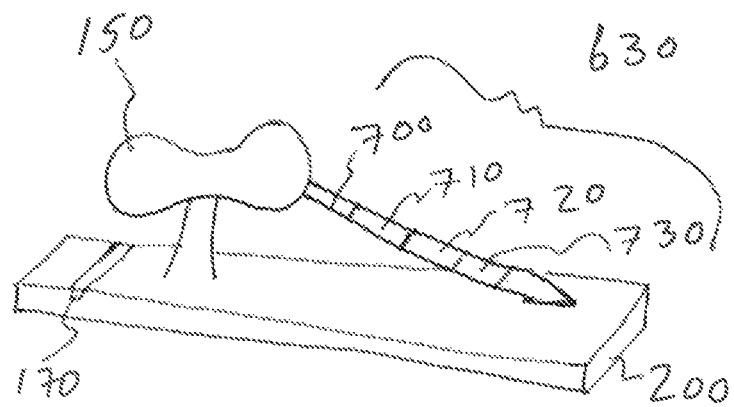
FIGS. 38, 39, 40, and 41 show a resonator and a polymer strand, each according to embodiments described herein.

FIG. 38 shows a microresonator 150, bus waveguide 170, and support 200. A polymer filament 630 is shown, having at least one region, for example a plurality of regions. The regions may include a binding region used to attach an analyte, spacer group, additional polymer filament, binding site and/or a perturbative member. For example, region 700 can be a spacer region, region 710 can be a binding region for binding an analyte, region 720 can be for binding a perturbative member, and region 730 can be a spacer region. Consider a single stranded DNA as the polymer filament: region 700 may include an attachment functionalization for attachment to the resonator (directly or indirectly such as through an optical handle); region 730 may also include an attachment functionalization for attachment to the support 200 or may indirectly attach to the support; region 710 may code for a DNA which is to be detected; region 720 is complementary to a DNA attached to a perturbative member such as a gold nanoparticle, core-shell particle (e.g. one with a metal core or shell), gold nanorod, and/or an irregular gold particle such as a star; region 730 may attach to a complementary DNA strand disposed on the surface, or may be functionalized so as to attach directly or indirectly to the substrate.

It is contemplated to use covalent crosslinks such as interstrand crosslinks (e.g. by the use of site specific (interstrand) crosslinking agents), particularly between regions that code for attachment of a perturbative member to the filament 630 and/or attachment to the substrate and/or waveguide to provide robust attachments that may resist the effects of heat which may otherwise increase the chance of separation of the strands. It is further contemplated that the binding region (e.g. 710) can be complementary to an analyte for example if the analyte is a DNA sequence, however it is also contemplated that the binding region (e.g. 710) can be attached to a complementary strand of DNA which is itself covalently attached to a binding site for attachment of an analyte. It is also possible for an additional spacer region between the binding region and the region for binding the perturbative member.

As described above, the binding region for the analyte lies between the perturbative member and the resonator, however a geometry in which the perturbative member lies between the binding region and the resonator is also contemplated. In the first instance, the binding region may be exposed to a greater field from the resonator which may increase sensitivity by a greater perturbative effect of the analyte when it is bound; in the second instance, there may be less heating effects on the binding region which may increase sensitivity by allowing for a stronger binding action between the analyte and the binding site.

Figure 39:
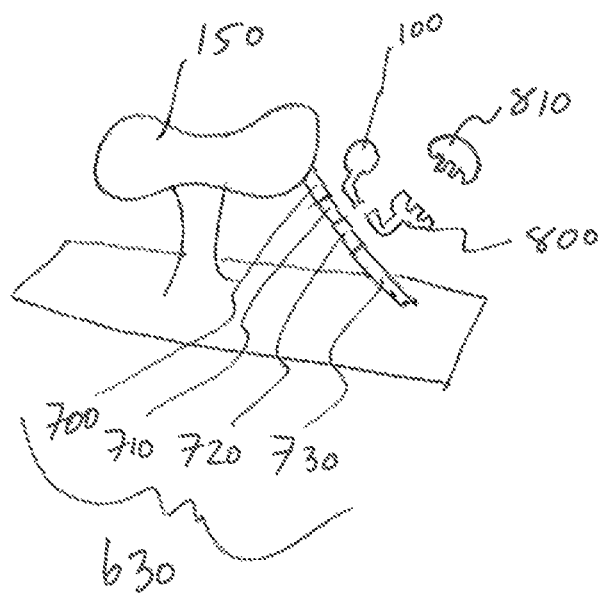

FIG. 39 shows a DNA strand 630 attached to a resonator 150. Region 700 of the DNA strand is attached to the resonator and provides a spacer. Region 710 codes for attachment of a DNA strand attached to a perturbative member 100. Region 720 codes for attachment of a DNA strand attached to a binding site 800, the binding site 800 acting to bind an analyte 810. As described previously, there can be a bus waveguide, and the DNA strand 630 can be attached to the resonator and the substrate. It is contemplated that the spacer 700 closest to the resonator provides a gap between the resonator's nearest surface and the perturbative member, which is aided by attachment of the far end of the DNA such as by an end region. A gap between the nearest surface of the waveguide 150 or waveguide assembly 160 (optionally including a coating) and the perturbative member can be at least about 1 nm, or 2 nm, 3 nm, 4 nm, 5 nm, 6, 7, 8, 9, or 10 nm, or 12, 14, 16, 18, or 20 nm, or 25, 30, 35, 40, 45, 50 55, 60, or 70, 80, 90, 100, 120, 140, 160, 180, 200, or from 200 to 500 nm, or 500 to 1000 nm.

It is contemplated that, as shown in FIG. 39, region 720 may be coded such that it is selectively amenable for interstrand covalent crosslinking, particularly if region 720 is to be used to attach a perturbative member. Additionally, if a more stable binding site 800 is desirable, then region 720 can also be amenable to interstrand covalent crosslinking. However, it may be desirable that the region 720 be used as a programmable binding region, so that a binding site/DNA pair 800 can be reversibly attached (e.g. the pair is attached, used for detection of an analyte 810, and subsequently removed by for example DNA denaturation, and replaced with a different binding site attached to the same DNA code which binds to region 720).

Figure 40:
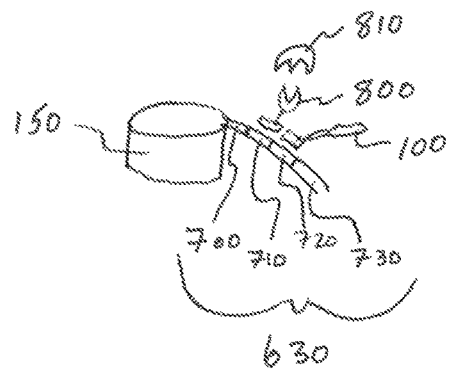

In FIG. 40, the arrangement is such that the binding site 800 is disposed between the perturbative member 100 and the resonator 150. There is optionally a spacer between the region 710 which binds the binding site 800 and the region 720 which binds the perturbative member 100. It is contemplated that region 720 may be amenable to selective interstrand crosslinking, for the same reasons as discussed above. In other words, the perturbative member 100 may be covalently attached to the polymer filament 630. Alternatively or additionally, the binding region 710 of FIG. 40 can be covalently crosslinked to the binding site 800.

Figure 41:
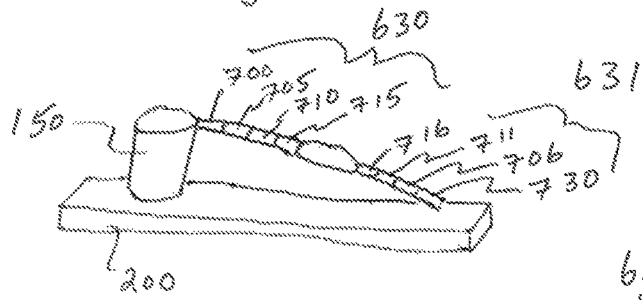

FIG. 41 shows a perturbative member 100 which is disposed between two polymer filaments 630 and 631, the polymer filaments attached to the perturbative member through two attachment regions 715 and 716, respectively. Region 710 and/or region 711 may be binding regions such as for an additional perturbative member(s) and/or analyte binding region. Regions 700 and 730 can attach the respective polymer filaments 630 and 631 to the resonator 150 and substrate 200 (e.g. 200 and/or 210). An embodiment in which the binding region for the analyte is disposed so as to avoid contact with a surface, particularly those of the microresonator 150 and substrate 200, is contemplated, an effect of which is to reduce steric hindrance of the binding site, irreversible denaturation (unfolding) of the binding site, and/or increase the availability of the binding site to a surrounding medium such as a solvent in which an analyte may be solvated and/or dispersed. The polymer filaments may be DNA, particularly single stranded DNA with coded regions coding for different regions, e.g. 705, 710, 711, 706. End regions, e.g. 700, 730 may be end functionalized to promote covalent binding to other structures such as the resonator or substrate; furthermore, regions 715, 716 for attachment to the perturbative member 100 may be end functionalized. Alternatively or additionally, end regions and attachment regions may include DNA code which is particularly amenable for interstrand crosslinking, e.g. to DNA strands attached to the resonator, perturbative member(s), and/or substrate.

Figure 42:
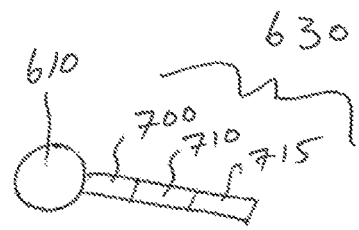
FIG. 42 shows an optical handle and a polymer strand, according to embodiments described herein.
Figure 43:
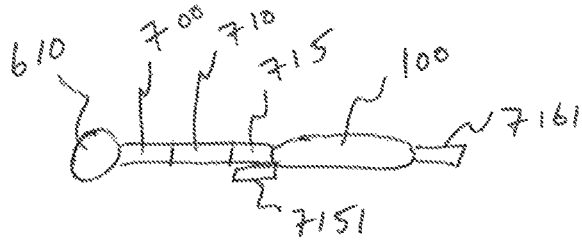
FIGS. 43 and 44 show an optical handle, a polymer strand, and a perturbative member, each according to embodiments described herein.

FIG. 42 shows an optical handle 610, functionalized with a polymer strand 630 such as a single stranded DNA having regions 700, 710, and 715. Region 700 may serve as an attachment region for attachment to the optical handle and can be end-functionalized so as to covalently attach to the optical handle 610. Region 710 may be a spacer and/or may serve as a binding region 710, e.g. for the analyte. Region 715 may serve as an attachment site for a perturbative member such as a DNA functionalized nanoparticle, core-shell particle, etc. Region 715 may particularly be amendable to covalent interstrand crosslinking By mixing the species depicted in FIG. 42, which can be colloidally dispersed, with colloidally dispersed perturbative members, a colloidally dispersed structure such as that shown in FIG. 43 can be obtained and/or isolated. For example, the perturbative member is functionalized with DNA 7151 complementary to region 715. Region 7151 can bind to region 715, which can attach the perturbative member 100 to the optical handle 610. It is possible that a second region 7161 attached to the perturbative member 100 is not complementary to region 715, thus remaining free. Alternatively or additionally, stoichiometric control may yield for example: a mixture or mainly the species depicted in FIGS. 42 and 43 (e.g. using a stoichiometric excess of the species of FIG. 42 mixed with the DNA functionalized perturbative member 100); or, using excess DNA functionalized perturbative member 100, a mixture of perturbative member and the species of FIG. 43. It is possible to isolate the species of FIG. 43 by for example centrifugation, gradient centrifugation, by exploiting dielectrophoresis and/or electrophoresis (e.g. (asymmetric) field flow fractionization), and affinity and/or size exclusion chromatography. Sorting with optical tweezers may also be possible. Furthermore, addition of the species depicted in FIG. 42, or one like it, to that of FIG. 43 can yield the isolatable species depicted in FIG. 44.

Figure 44:
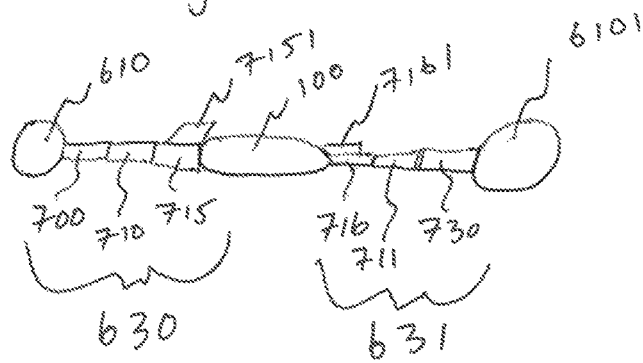

FIG. 44 depicts a perturbative member 100 attached to two polymer strands 630 and 631 by the use of for example single DNA strands 7151 and 7161 which are complementary to strands 715 and 716 which are attached to optical handles 610 and 6101. Embodiments which have more than two optical handles attached to a perturbative member, particularly through polymer strands such as DNA, are also contemplated. The optical handles can be useful in placement of the assembly onto desired locations within a device, particularly a device exploiting perturbation of an electromagnetic field by the perturbative member 100, such as in response to binding of an analyte to for example a binding region which may be region 710 and/or region 711, which are optionally DNA sequences that code for the same binding agent or different binding agents.

Figure 45:
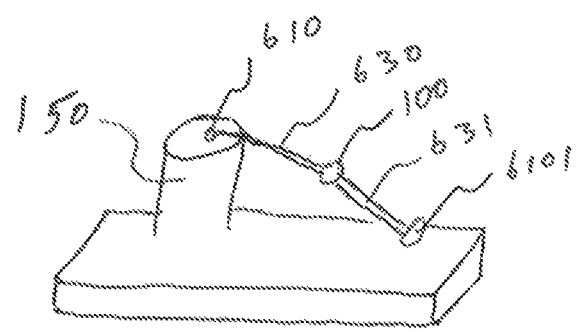
FIG. 45 shows a perturbative member, polymer strands, and a resonator, according to embodiments described herein.

FIG. 45 shows a resonator 150 with a perturbative member 100 supported by polymer strands 630 and 631. Attachment of the polymer strands, particularly such that the perturbative member is disposed away from any surfaces is facilitated by the use of optical handles 610 and 6101. Optical tweezers can be used to place the optical handles at surfaces: for example handle 6101 is attached to the substrate 200, and the strands 630 and 631 are stretched (although any tension in the strand is optional) by handle 610 which is subsequently attached near the resonator, such as in the interior of the top face of a disc resonator 150.

Figure 46:
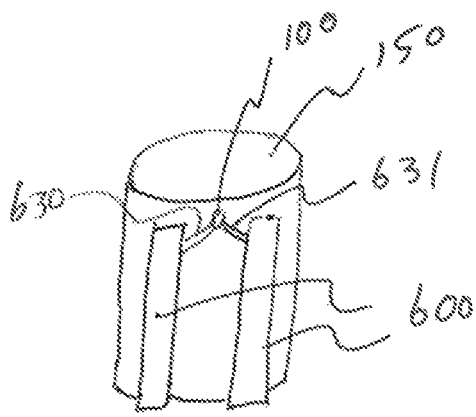
FIGS. 46 and 47 shows a perturbative member supported by posts and a resonator, each according to embodiments described herein.
Figure 47:
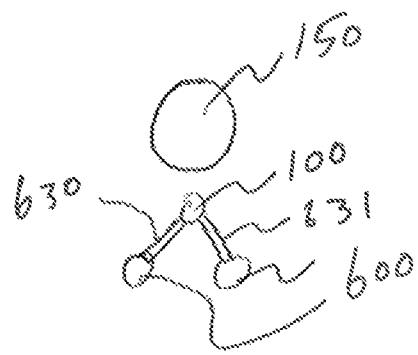

FIG. 46 shows a perturbative member 100 supported by two posts 600, disposed so as to make a gap between the resonator 150 and the perturbative member 100. Either or both of the posts 600 can optionally be actuatable, i.e. movable, so as for example to adjust the gap distance and/or magnitude of a force provided by tension of polymer strands 630 and 631 particularly if the perturbative member 100 is attracted to the resonator 150 by an optical field gradient. FIG. 47 shows another view of the perturbative member 100 supported by two posts 600. The tensile force provided by the polymer strand(s) may oppose the optical gradient force.

Figure 48:
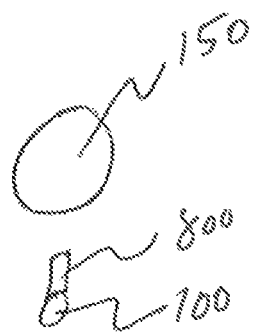
FIG. 48 shows a perturbative member, a binding region, and resonator, according to embodiments described herein.

FIG. 48 shows a perturbative member 100 disposed away from a nearest surface of a resonator 150, the perturbative member 100 having a binding region 800 attached to it. The binding region may be disposed between the resonator 150 and the perturbative member as depicted. There may be multiple binding regions attached to the perturbative member.

In an embodiment, the perturbative member, for example a metal part thereof, has a volume of approximately $4 \times R^3$ wherein R is from 1 to 1000 nm, particularly 1 to 500 nm, more particularly from 10 to 100 nm, and more particularly 15 to 20 nm.

A method of operating an optical device is envisioned, comprising: inputting an input EM wave such that the input EM wave optically couples to a microresonator and a supported EM wave is formed which is supported by the microresonator; perturbing the supported EM wave by a perturbative member located across a gap from a nearest surface of the microresonator; outputting the supported EM wave to form an output EM wave; and detecting the output EM wave; optionally modulating the perturbative member such as driving a mechanical oscillation of the perturbative member; wherein optionally modulating the perturbative member includes modulating the input EM wave such that the perturbative member is modulated; optionally modulating, such as pulsing, the input EM wave such that the position of the perturbative member is modulated; optionally binding an analyte near the perturbative member; wherein optionally detecting the output EM wave includes mixing the output EM wave with a reference EM wave such as the input EM wave; optionally positioning the perturbative member, particularly adjusting the gap; wherein optionally positioning the perturbative member is with an actuator and/or an intensity such as a continuous wave intensity component of the input EM; wherein optionally the output EM wave is modulated by the perturbative member, such as by a mechanical and/or quantum mechanical oscillation thereof; wherein optionally the output EM wave is perturbed by an analyte, such as an analyte bound to a binding site. For example, a mechanical resonance of the perturbative member is such that a quantum mechanical and/or plasmon resonance of the perturbative member is co-resonant with a supported EM mode of the resonator, particularly when the perturbative member is located at at least one position among the positions sampled by the perturbative member in a complete oscillation of the mechanical mode of the perturbative member. Optionally, the mechanical mode of the perturbative member is such that there exist positions where the quantum mechanical and/or plasmon resonance of the perturbative member is also not co-resonant with the supported EM mode of the resonator. The perturbative member can be stiff, in some embodiments, such as to undergo minimal displacement, even if the energy of the supported EM mode of the resonator is modulated. For example, modulation can be induced by expansion and contraction of the resonator as the intensity of the supported EM mode is modulated.

Herein, a "binding region" or "binding site" can optionally include a surface for adsorption of an analyte and can include a porous media, including a porous micro- or nanoparticle, and can also include a biochemical binding region/site such as at least a portion of a single strand of DNA including optionally end-functionalized DNA, RNA, and proteins, particularly conjugated immunoproteins. DNA is about 3.4 nm per 10 base pairs.

Herein a perturbative member can perturb an EM wave supported by a waveguide such as a waveguide of a resonator, microresonator, waveguide assembly, or the like. The EM wave can be perturbed by intensity (such as by inducing scattering and/or perturbing the local refractive index), shifting a resonance frequency, shifting a polarization state, and/or phase-shifting, to name a few examples. Herein, a perturbative member can include a nitrogen vacancy center, for example in a carbon matrix such as a carbon film or nanoparticle such as one having a diamond nanostructure.

Herein, a "travelling wave" such as one supported by a waveguide may be one travelling wave of a plurality of travelling waves, such as a plurality including an oppositely directed travelling wave. A combination of two travelling waves of opposite direction may result, for example, in a standing wave, such as a standing wave supported by a waveguide.

Herein "actuable" can mean movable such as by the use of an actuator such as a piezoelectric actuator.

The above description is intended to be illustrative. The above-described embodiments may be used in combination with each other. Many other embodiments will be apparent to those of skill in the art upon reviewing the above description. While certain exemplary embodiments have been described in detail and shown in the accompanying drawings, it is to be understood that such embodiments are illustrative. The scope of the invention therefore should be determined with reference to the appended claims, along with the full scope of equivalents to which such claims are entitled.

I claim:

1. An electromagnetic waveguide assembly comprising:
    a microresonator for supporting an electromagnetic wave, the microresonator including a waveguide,
    a perturbative member configured to be within an evanescent region, provided by the waveguide, which extends beyond a boundary of the waveguide of the microresonator, the perturbative member configured for perturbing the electromagnetic wave,
    a substrate which supports the perturbative member and the microresonator, and
    a gap between a nearest surface of the perturbative member and a nearest surface of the microresonator, the nearest surfaces being the nearest surfaces of the respective perturbative member and the microresonator to each other; wherein
    the nearest surface of the microresonator to the perturbative member is curved; and wherein
    the microresonator is monolithically constructed on the substrate or is fixed by an adhesive to the substrate.

2. The electromagnetic waveguide assembly according to claim 1, wherein
    the gap distance is adjustable.

3. The electromagnetic waveguide assembly according to claim 1, wherein
    the nearest surface of the microresonator to the perturbative member is curved with a curvature greater than a farther surface of the microresonator.

4. The electromagnetic waveguide assembly according to claim 1, wherein
    the nearest surface of the microresonator to the perturbative member is curved with a curvature greater than the average curvature of the microresonator.

5. The electromagnetic waveguide assembly according to claim 2, wherein
    the position of the perturbative member is adjustable in a radial direction about a center axis of the microresonator by an actuator which is fixed by an adhesive to the substrate.

6. The electromagnetic waveguide assembly of claim 1, wherein
    the microresonator includes an optically active media disposed asymmetrically such that a concentration of an optically active media in a region near the perturbative member is greater or lesser than a concentration of the optically active media in a region farther from the perturbative member; wherein the optically active media is for generating an optical signal.

7. The electromagnetic waveguide assembly of claim 6, wherein
    the region of the microresonator near the perturbative member has a greater or lesser concentration of the optically active media in comparison to the average concentration of the optically active media of the microresonator.

8. The electromagnetic waveguide assembly of claim 1, wherein
    the perturbative member includes at least one of a plasmon supporting metal nanoparticle, a metal film, a nanowire, and a nanorod.

9. The electromagnetic waveguide assembly of claim 1, further comprising
    a plasmon supporting member disposed on the surface of the microresonator near the perturbative member.

10. The electromagnetic waveguide assembly of claim 8, wherein
a long axis of the perturbative member is oriented radially outwardly from the center of the microresonator.

11. The electromagnetic waveguide assembly of claim 2, further comprising
an actuator for adjusting a position of the perturbative member; wherein
the actuator is fixed by an adhesive to the substrate.

12. A waveguide assembly comprising:
a waveguide for supporting an electromagnetic wave, and
a polymer filament;
the polymer filament including a molecularly coded region for binding a complementarily molecularly coded species;
the coded region disposed at a distance from a nearest surface of the waveguide, the distance being greater than 1 nm;
the coded region disposed within an evanescent region, provided by the waveguide, which extends beyond a boundary of the waveguide.

13. The waveguide assembly according to claim 12, further comprising
a perturbative member attached to the polymer filament.

14. The waveguide assembly according to claim 13, wherein
the perturbative member is covalently attached to the polymer filament.

15. The electromagnetic waveguide assembly of claim 1, wherein
the microresonator has an angled region near the perturbative member.

16. The electromagnetic waveguide assembly of claim 1, wherein
the nearest surface of the microresonator has a smaller radius of curvature than the waveguide elsewhere.

17. The electromagnetic waveguide assembly of claim 1, wherein
the microresonator includes a gain media disposed asymmetrically such that a concentration of the gain media in a region near the perturbative member is greater or lesser than a concentration of the gain media in a region farther from the perturbative member.

18. The electromagnetic waveguide assembly of claim 1, wherein
a region of the microresonator near the perturbative member has a greater or lesser concentration of a gain media in comparison to the average concentration of the gain media of the microresonator.

19. The electromagnetic waveguide assembly of claim 1, further comprising
a bus waveguide for coupling with the microresonator; wherein
the perturbative member is monolithically constructed on the substrate or is fixed by an adhesive to the substrate; wherein
the microresonator is configured to support an optical frequency whispering gallery mode; and wherein
the perturbative member includes at least one of a metal film, a metal nanoparticle, a nanorod, and a nanowire.

20. The electromagnetic waveguide assembly of claim 1, further including a coating on the waveguide.

* * * * *